United States Patent [19]

DiCosimo et al.

[11] Patent Number: 4,603,207
[45] Date of Patent: Jul. 29, 1986

[54] CONVERSION OF A MIXTURE OF 3-METHYLPYRIDINE AND 3-METHYLPIPERIDINE TO 3-CYANOPYRIDINE

[75] Inventors: Robert DiCosimo, Shaker Heights; James D. Burrington, Richmond Heights; Dev D. Suresh, Macedonia, all of Ohio

[73] Assignee: The Standard Oil Company, Cleveland, Ohio

[21] Appl. No.: 791,033

[22] Filed: Oct. 24, 1985

[51] Int. Cl.[4] ............................................ C07D 213/60
[52] U.S. Cl. .................................................... 546/286
[58] Field of Search ......................................... 546/286

[56] References Cited

FOREIGN PATENT DOCUMENTS 1169864  6/1984  Canada ................................. 546/286

Primary Examiner—Henry R. Jiles
Assistant Examiner—J. Richter
Attorney, Agent, or Firm—Charles S. Lynch; John E. Miller; Larry W. Evans

[57] ABSTRACT

Disclosed is the vapor phase, catalytic reaction of a mixture of 3-methylpyridine and 3-methylpiperidine with ammonia and molecular oxygen to make 3-cyanopyridine.

7 Claims, No Drawings

CONVERSION OF A MIXTURE OF 3-METHYLPYRIDINE AND 3-METHYLPIPERIDINE TO 3-CYANOPYRIDINE

This invention relates to the catalytic reaction of a mixture of 3-methylpyridine and 3-methylpiperidine with molecular oxygen and ammonia to produce 3-cyanopyridine.

3-methylpyridine can be ammoxidized to 3-cyanopyridine in the presence of certain catalysts containing P, V, Mo and oxygen with excellent yields. In the course of an investigation we attempted to react 3-methylpiperidine with oxygen and ammonia in the presence of such a catalyst but obtained only very low yields and selectivity to 3-cyanopyridine, even though considerable 3-methylpyridine was made.

We have now discovered that when a mixture of 3-methylpyridine and 3-methylpiperidine are reacted with molecular oxygen and ammonia in the vapor phase under reaction conditions suitable for ammoxidation of 3-methylpyridine over the same catalysts, very high yields and selectivity of the 3-methylpyridine to 3-cyanopyridine are still maintained and, surprisingly, the yields of 3-methylpiperidine to 3-cyanopyridine are also greatly increased when the mole ratio of the 3-methylpyridine to 3-methylpiperidine in the feed initially contacting the catalyst is at least 3:1, especially when this ratio is at least 4:1.

Thus, according to the present invention there is provided a process for making 3-cyanopyridine which comprises contacting and reacting in the vapor phase a feed mixture containing molecular oxygen, ammonia, 3-methylpyridine and 3-methylpiperidine with a solid catalyst which is a complex oxide having the elements and the amounts thereof indicated by the empirical formula $$P_a V_b Mo_c M_d O_x$$

wherein M is one or any number more of Sb, Fe, W, Cu, K, Cs, B, Te, Sn, Mn, Nb, U, Bi and Cr and a=0.1–3,
b=0.1–6,
a+b=at least 1.5,
c=12,
d=0–4, and x is a number sufficient to satisfy the valence requirements of other elements present, said contacting being effected under reaction conditions suitable for ammoxidizing 3-methylpyridine over such catalysts, wherein the feed initially contacting the catalyst contains a molar ratio of 3-methylpyridine to 3-methylpiperidine of at least 3:1, especially when this ratio is at least 4:1.

In the foregoing catalysts, usually a is 0.2–3 and b is 0.5–4.

The catalysts of the invention as noted above can optionally be mixed with or deposited on a support such as silica, silica-alumina, alumina, zirconia, titanium dioxide and the like. The active catalyst defined above can be 1–100 percent of the solid catalyst.

Air is a convenient source of molecular oxygen, although oxygen per se can be used, or air that is diluted with additional nitrogen.

While such suitable reaction conditions are not the heart of the present invention, the usual reaction conditions are 350°–460° C., more usually 365°–420° C., pressure 0.8 to 1.5 atmospheres, although higher or lower pressures can be used; contact time 0.1 to 20 seconds, usually 0.5 to 10 seconds; and molar feed ratios per mole of combined heterocyclic substrate, 3–12, usually 4–10, $NH_3$; 2.5–7, usually 3–5, molecular oxygen. Suitable catalyst reactor types include a fixed reactor or a reactor in which a solid bed of particulate catalyst flows downwardly countercurrent to the feed gases.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 250° C. and 600° C. This calcination can take place outside of the catalytic reactor or an in situ activation can be utilized.

The following examples of the invention are merely illustrative and are not to be considered as limiting.C

EXAMPLE 1

Into a 1 L beaker containing 400 mL of distilled $H_2O$ was added 11.7 g (0.100 mol) of $NH_4VO_3$ and the resulting mixture heated to 80° C. with stirring. To this mixture was added 3.8 g (0.33 mol) of 85 percent $H_3PO_4$, and the mixture turned from a cloudy white suspension to a clear red solution. This solution was added at 80° C. with stirring to a mixture of 70.6 g (0.057 mol) of $(NH_4)_6Mo_7O_{24}\cdot 4H_2O$ in 250 mL of distilled $H_2O$ also at 80° C. To the resulting clear red solution was added 43.0 g of Nalco 2327 silica sol (40 percent $SiO_2$), and the resulting mixture boiled down to ca. 200 mL with vigorous stirring. When the mixture could no longer be stirred, it was heated at 120° C. for 16 hours, 290° C. for 3.0 hours, 425° C. for 16 hours, and finally at 540° C. for 4.0 hours, and the resulting brown solid ground and screened to 20–35 mesh. This catalyst has the empirical formula 80% $PV_3Mo_{12}O_x$ 20% $SiO_2$. The $SiO_2$ is of course the support.

EXAMPLE 2

A mixture of 14.5 g (49.8 mmol) of $Sb_2O_3$ and 60 mL of 70 weight percent $HNO_3$ was heated to 80° C. with stirring for 0.5 hours, then added to a slurry of 7.8 g (67.0 mmol) of $NH_4VO_3$ in 300 mL of $H_2O$ with stirring at 80° C. The resulting mixture was added with stirring to a mixture of 70.6 g (57.1 mmol) of $(NH_4)_6Mo_7O_{24}\cdot 4H_2O$, 0.95 g (8.33 mmol) of 85 weight percent $H_3PO_4$, and 67.1 g of 30 weight percent silica sol (Ludox A.S.) in 250 mL of $H_2O$ at 80° C. Stirring and heating were continued until the mixture started to gel, then the mixture was heated at 130° C. for 16 hours, 425° C. for 16 hours, and finally at 650° C. for 3 hours. The resulting solid was ground and screened to 20–35 mesh. It was 80 percent active ingredient of the formula $P_{0.25}V_2Sb_3Mo_{12}O_x$ and 20% $SiO_2$ support.

The following ammoxidation runs were performed in a 5 cc. tubular steel microreactor equilibrated in a salt bath at the desired reaction temperature. The catalyst was placed in the microreactor tube between 2 layers of pyrex glass wool. The organic substrate was fed by syringe using an Orion Research Sage Pump. Air and ammonia flow rates were controlled by either a Brooks Dual-Channel or a Tylan Mass Flow Controller.

EXAMPLE 3

2.0 cc of 80% $PV_3Mo_{12}O_x$. 20% $SiO_2$ catalyst of Example 1 was placed in the microreactor and equilibrated at 405° C., then a gaseous mixture of 1.0 3-methylpiperidine:7.5 $NH_3$:19.9 air (mole ratios) was fed through the reactor using a contact time of 4.0 seconds. After 5 hours on stream the conversion of the substrate was 100 percent, selectivity to 3-cyanopyridine was 6.4 percent and selectivity to 3-methylpyridine was 52.8 percent.

In this and all other examples the amounts of heteroaromatic nitrile and 3-methylpyridine products and of unreacted heteroaromatic substrate were determined by collecting the reactor effluent in a scrubber containing 10 mol of toluene at 0° C., and analyzing the resulting solution by g.c. on a 30-meter×0.32 mm ID capillary BP-10 column, using undecane as internal standard.

EXAMPLE 4

2.0 cc of 80% $PV_3MO_{12}O_x$.20% $SiO_2$ catalyst of Example 1 was placed in the microreactor and equilibrated at 405° C., then a gaseous mixture of 1.0 3-methylpiperidine:2.5 $NH_3$:13.3 air was fed through the reactor using a contact time of 4.5 seconds. After 3 hours on stream the substrate was 100 percent, selectivity to 3-cyanopyridine was 5.5 percent and selectivity to 3-methylpyridine was 49.3 percent.

EXAMPLE 5

2.0 cc of 80% $PV_3MO_{12}O_x$.20% $SiO_2$ catalyst of Example 1 was placed in the microreactor and equilibrated at 405° C., then a gaseous mixture of 1.0 3-methylpiperidine:4.3 $NH_3$:13.1 air was fed through the reactor using a contact time of 4.5 seconds. The conversion of the substrate was 100 percent, selectivity to 3-cyanopyridine was 5.1 percent and selectivity to 3-methylpyridine was 58.2 percent.

EXAMPLE 6

2.0 cc of 80% $PV_3MO_{12}O_x$.20% $SiO_2$ catalyst of Example 1 was placed in the microreactor and equilibrated at 405° C., then a gaseous mixture of 0.82 3-methylpyridine:0.18 3-methylpiperidine:7.5 $NH_3$:19.9 air was fed through the reactor using a contact time of 6.4 seconds. Conversion of the methylpiperidine was 100 percent and conversion of the methylpyridine was 93 percent. For each mole of combined 3-methylpiperidine plus 3-methylpyridine fed was obtained 0.853 mole of 3-cyanopyridine. If it be assumed that all of the converted 3-methylpyridine formed 3-cyanopyridine, the minimum selectivity of 3-methylpiperidine to 3-cyanopyridine was 50 percent.

EXAMPLE 7

2.0 cc of 80% $PV_3MO_{12}O_x$.20% $SiO_2$ catalyst of Example 1 was placed in the microreactor and equilibrated at 405° C., then a gaseous mixture of 0.83 3-methylpyridine:0.17 3-methylpiperidine:8 $NH_3$:21.5 air was fed through the reactor using a contact time of 6.4 seconds. Data taken after 68 hours showed that conversion of the 3-methylpiperidine was 100 percent and conversion of the 3-methylpyridine was 94.7 percent. For each mole of combined 3-methylpiperidine plus 3-methylpiperidine fed there was obtained 0.861 mole of 3-cyanopyridine. If it be assumed that all of the converted 3-methylpyridine formed 3-cyanopyridine, the minimum selectivity of 3-methylpiperidine to 3-cyanopyridine was 44.1 percent.

EXAMPLE 8

When Example 6 is repeated but using the catalyst of Example 2, similar results are obtained.

EXAMPLE 9

2.0 cc of 80% $PV_3MO_{12}O_x$.20% $SiO_2$ catalyst of Example 1 was placed in the microreactor and equilibrated at 405° C., then a gaseous mixture of 0.83 methylpyridine:0.17 3-methylpiperidine:8 $NH_3$:21.5 air was fed through the reactor using a contact time of 6.4 seconds. Data taken after 162 hours showed that conversion of the 3-methylpiperidine was 100 percent and conversion of the 3-methylpyridine was 95.5 percent. For each mole of combined 3-methylpiperidine plus 3-methylpyridine fed there was obtained 0.89 mole of 3-cyanopyridine. If it be assumed that all of the converted 3-methylpyridine formed 3-cyanopyridine, the minimum selectivity of 3-methylpiperidine to 3-cyanopyridine was 57 percent.

EXAMPLE 10

2.0 cc of 80% $PV_3MO_{12}O_x$.20% $SiO_2$ catalyst of Example 1 was placed in the microreactor and equilibrated at 405° C., then a gaseous mixture of 0.465 3-methylpyridine:0.535 3-methylpiperidine:7.2 $NH_3$:19.1 air was fed through the reactor using a contact time of 4 seconds. Conversion of the 3-methylpiperidine plus 3-methylpiperidine was only 57.3 percent. The yield of 3-cyanopyridine based on the combined feeds was only 35.3 percent, with a selectivity of 61.6 percent. This example, outside the invention, shows that the advantages of the invention are not obtained when the feed contains too much 3-methylpiperidine.

As will be evident to those skilled in the art various modifications of this invention can be made or followed in the light of the foregoing disclosure and discussion without departing from the spirit and scope of the disclosure or from the scope of the claims.

We claim:

1. A process for making 3-cyanopyridine which comprises contacting and reacting in the vapor phase a feed mixture containing molecular oxygen, ammonia, 3-methylpyridine and 3-methylpiperidine with a solid catalyst which is a complex oxide having the elements and the amounts thereof indicated by the empirical formula $$P_a V_b Mo_c M_d O_x$$

wherein M is one or any number more of Sb, Fe, W, Cu, K, Cs, B, Te, Sn, Mn, Nb, U, Bi and Cr and a=0.1–3,
b=0.1–6,
a+b=at least 1.5,
c=12,
d=0–4, and x is a number sufficient to satisfy the valence requirements of other elements present, under the reaction conditions suitable for ammoxidizing 3-methylpyridine over such catalysts, wherein the feed initially contacting the catalyst contains a molar ratio of 3-methylpyridine to 3-methylpiperidine of at least 3:1.

2. A process according to claim 1 wherein a is 0.2–3 and b is 0.5–4.

3. A process according to claim 1 wherein the molar ratio of 3-methylpyridine to 3-methylpiperidine is at least 4:1.

4. A process for making 3-cyanopyridine which comprises contacting and reacting in the vapor phase a feed mixture containing molecular oxygen, ammonia, 3-methylpyridine and 3-methylpiperidine with a solid catalyst which is a complex oxide having the elements and the amounts thereof indicated by the empirical formula $$P_a V_b Mo_c M_d O_x$$

wherein M is one or any number more of Sb, Fe, W, Cu, K, Cs, B, Te, Sn, Mn, Nb, U, Bi and Cr and a=0.1–3,
b=0.1–6,
a+b=at least 1.5,
c=12,
d=0–4, and x is a number sufficient to satisfy the valence requirements of other elements present, under the reaction conditions suitable for ammoxidizing 3-methylpyridine over such catalysts, wherein the feed initially contacting the catalyst contains a molar ratio of 3-methylpyridine to 3-methylpiperidine of at least 3:1, wherein the mole ratios in the feed to the reaction zone of (3-methylpyridine+3-methylpiperidine):NH$_3$:molecular oxygen are in the range 1:3–12:2.5–7.

5. A process of claim 4 wherein the mole ratios in the feed to the reaction zone of (3-methylpyridine+3-methylpiperidine):NH$_3$: molecular oxygen are in the range 1:4–10:3–5.

6. A process according to claim 4 wherein a is 0.2–3 and b is 0.5–4.

7. A process according to claim 4 wherein the molar ratio of 3-methylpyridine to 3-methylpiperidine is at least 4:1.

* * * * *